US00PP30347P2

(12) United States Plant Patent
Hansen

(10) Patent No.: US PP30,347 P2
(45) Date of Patent: Apr. 2, 2019

(54) ***MONARDA* PLANT NAMED 'ELECTRIC NEON PINK'**

(50) Latin Name: *Monarda hybrida*
Varietal Denomination: Electric Neon Pink

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/932,528

(22) Filed: Mar. 12, 2018

(51) Int. Cl.
*A01H 5/02* (2018.01)

(52) U.S. Cl.
USPC ..... Plt./455

(58) Field of Classification Search
USPC ..... Plt./455
See application file for complete search history.

*Primary Examiner* — Annette H Para

(57) ABSTRACT

The new and distinct cultivar of ornamental cultivar of ornamental Bee Balm named *Monarda* 'Electric Neon Pink' is winter-hardy and has rapidly-growing, short, tightly clumping habit with dark green foliage, numerous large neon-pink flowers and resistant to powdery mildew and useful for the garden landscape.

1 Drawing Sheet

Botanical designation and cultivar denomination:
Botanical classification: *Monarda hybrida.*
Variety denomination: 'Electric Neon Pink'.

BACKGROUND OF THE INVENTION

The present invention relates to the new and distinct cultivar of bee balm, botanically known as *Monarda hybrida* 'Electric Neon Pink', and hereinafter also referred to by the cultivar 'Electric Neon Pink' or the "new plant". The new plant was the subject of cross by the inventor in the summer of 2013 at a wholesale perennial nursery in Zeeland, Mich., USA. Seed was harvested by the inventor on Oct. 29, 2013 and the individual seedling later assigned the breeder identification number 13-134-2. The female or seed parent is a proprietary unreleased hybrid known by the breeder code 12-27-1 (not patented) and the male or pollen parent is a proprietary, unnamed, unreleased hybrid between 'Burgundy Bunny' (not patented) times an unnamed proprietary selection of *Monarda pringlei* (not patented). The plant was initially subjected to evaluation in the summer of 2014 in trial plots of the same nursery in Zeeland, Mich. The new plant was collected and set apart as a single selected seedling in July of 2014 and passed final evaluation in the summer of 2015.

The plant has been asexually propagated initially by division and later by stem cuttings at the same nursery at the greenhouses in Zeeland, Mich., and both asexually propagation methods have been found to produce plants stable and identical to the original selection.

BRIEF SUMMARY OF THE PLANT

'Electric Neon Pink' is unique from its parents and all other bee balm plants known to the inventor. The nearest comparison varieties are 'Rockin' Raspberry' U.S. Plant Pat. No. 28,752, 'Pink Lace' U.S. Plant Pat. No. 18,367 and 'Bubblegum Blast' U.S. Plant Pat. No. 27,497. 'Rockin' Raspberry' is slightly shorter in habit and has a flower color that is deeper purple than the new plant. 'Pink Lace' is shorter and has a flower color that is a lighter purplish-red. 'Bubblegum Blast' is nearly the same habit height and has a different petal color. The new plant also has darker reddish purple spots on the petals which the above plants do not. 'Leading Lady Lilac' U.S. Plant Pat. No. 26,431 and 'Leading Lady Plum' U.S. Plant Pat. No. 26,447 have darker spotted petals but are much shorter in habit and have lighter lavender petals and magenta-purple petal colors, respectively.

The female parent had purple flowers and was more compact. The male parent was taller, more reddish in flower color and a looser plant habit. Neither parent was maintained, so further comparison is not possible.

The following are traits of *Monarda* 'Electric Neon Pink' that in combination distinguish it from all other Bee Balm known to the inventor:

1. Moderate plant height, moderate growth rate, winter-hardy, tightly-clumping habit.
2. Dark-green, slightly shiny, powdery mildew resistant foliage.
3. Large neon-pink flowers for a long period in summer.

BRIEF DESCRIPTION OF THE DRAWINGS

The photographs of the new plant demonstrate the unique traits of 'Electric Neon Pink' and the overall appearance of the plant at two-years-old in a full sun trial garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
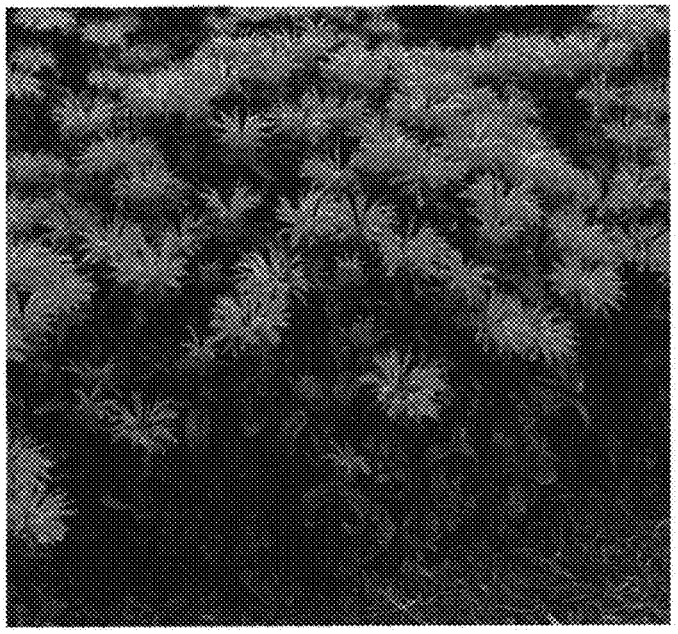
FIG. 1 shows the new plant in flower.
Figure 2:
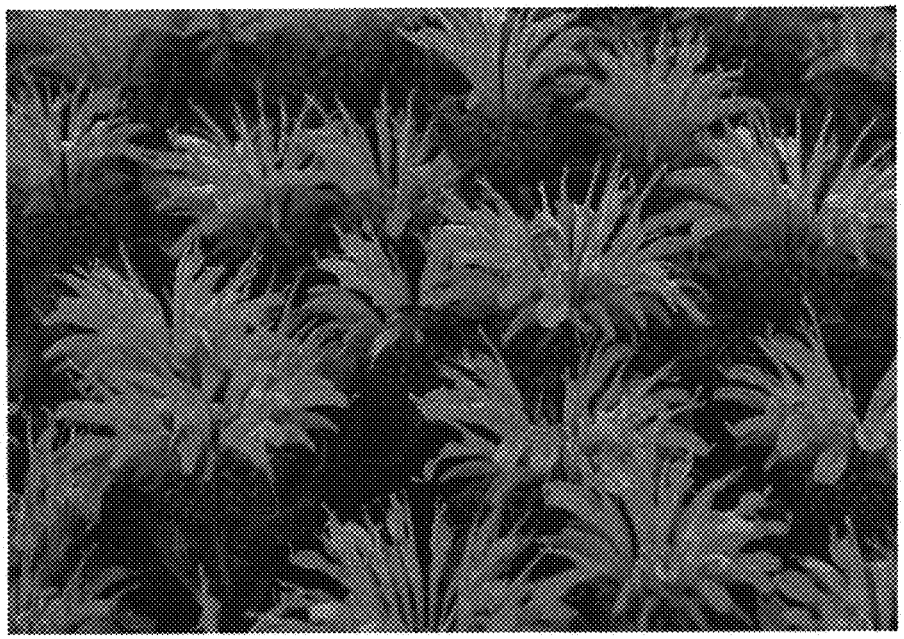
FIG. 2 shows a close-up of the flower.

The following descriptions and color references are based on the 2015 edition of The Royal Horticultural Society Colour Chart except where common dictionary terms are used. *Monarda* 'Electric Neon Pink' has not been observed under all possible environments. The phenotype may vary slightly with different growing environments such as temperature, light, fertility, soil pH, moisture and maturity levels, but without any change in the genotype. The following observations and size descriptions are based on two-year-old plants grown in full-sun in trial beds at a nursery in Zeeland, Mich. with minimal supplemental fertilizer and water as needed but without plant growth regulators or pinching.

Botanical classification: *Monarda hybrida;*

Parentage: Female (seed) parent is the proprietary hybrid known as 12-27-1 comprising *Monarda* 'Peter's Purple' (not patented) and possibly other unknown parents from the established breeding block, 'Peter's Purple' is reportedly a hybrid between *Monarda fistulosa* 'Claire Grace' (not patented) and an unnamed selection of *Monarda barlettii*; the male (pollen) parent is an unreleased hybrid between 'Burgundy Bunny' times a proprietary unnamed selection of *Monarda pringlei;*

Plant habit: Hardy herbaceous perennial, compact, producing several stems spreading by short rhizomes; about 60.0 cm tall at flowering and about 60.0 cm wide; flowering begins mid-summer in Michigan and continuing for about 3 to 4 weeks;

Propagation: Stem cuttings;

Time to produce finished crop in 3.8 liter pots: About 7 to 9 weeks; moderately fast rate of growth;

Root: Fine, fibrous and freely branching; color creamy white to tan depending on soil type;

Leaves: Simple; lanceolate; opposite; margin serrated; sparsely puberulent abaxial and adaxial; adaxial surface lustrous, semi-lustrous to matte abaxial; acute apex; rounded base; average about 8.0 cm long and about 2.5 cm wide;

Leaf color: Young adaxial surface nearest RHS 146D and abaxial nearest RHS 146C; mature leaves nearest RHS 139A adaxial and abaxial surface of mature leaves nearest RHS 137B;

Foliage fragrance: Pleasantly lemony;

Veins: Pinnate; glabrous adaxial; sparsely puberulent and costate abaxial;

Vein color: Adaxial midrib and proximal secondary veins nearest RHS 147D, distal secondary veins nearest RHS 139A; abaxial midrib nearest RHS 145C and secondary veins nearest RHS 147C;

Petiole: Concavo-convex; sparsely puberulent; margin sparsely ciliolate; average about 8.0 mm long and 2.0 mm across;

Petiole color: Nearest RHS 197D with light basal blush of nearest RHS 183A adaxial; between RHS 147D and RHS 147C abaxial with blush nearest RHS 183A;

Stems: Squared, sparsely puberulent, pubescent at nodes; 4.0 to 6.5 mm across at base, average about 5.0 mm across; about 40 stems per plant;

Stem color: Nearest RHS 144A;

Nodes: 11 per stem before flowers; pubescent; average internode length about 3.0 cm, closer at base; node color nearest RHS 147D;

Flowers: Single labiate flowers arranged in terminal globular head about 9.0 cm across and 3.5 cm tall opening from the center and progressing outwardly and down; persisting about 5 days in Michigan; numerous, about 180 flowers per head, 40 to 50 open at one time; self-cleaning;

Flower fragrance: Lightly musty;

Flower attitude: Initially upward toward center of head and becoming outwardly to slightly drooping in outer portion of head;

Buds one to two days prior to anthesis: Tubular arcuate, distally curved downward; about 3.2 cm long, basal one-third tubular about 1.0 mm diameter, mid-portion about 4.0 mm tall and 3.5 mm across;

Bud color one to two days prior to anthesis: Basal one-third nearest RHS NN155B; lower lip nearest RHS N57C with spots about 0.5 mm diameter of nearest RHS N200B; upper labium nearest RHS 61C;

Petals: Bilabiate, fused in basal 26.0 mm; upper hood slightly arcuate with sharply acute reflexed apex, puberulent abaxial and adaxial glabrous distally, adaxial tube puberulent; lower labium arcuate, with three distal lobes, center lobe emarginate apex, two side lobes with rounded apices;

Petal size: Upper hood to 4.0 cm long and 3.0 mm across and 3.0 mm tall at fusion; lower labium about 3.2 cm long with center lobe about 6.0 mm long and 2.0 mm wide at base, two side lobes about 1.0 mm long and 2.0 mm across; fused tube about 1.5 mm diameter;

Petal color: Upper hood abaxial nearest RHS 61C and adaxial between RHS 62B and RHS 62C; lower labium abaxial distal portion of center and side lobes nearest RHS N57D with spots of nearest RHS N200B, adaxial distal portion of center and side lobes nearest RHS 61C with spots of nearest RHS 60C; basal tube abaxial and adaxial nearest RHS NN155B;

Androecium: Two;

*Filaments*.—Two; terete; about 1.7 cm long by 1.0 mm diameter; color distally nearest RHS 73A, proximally blend between RHS 73C and RHS 75B.

*Anther*.—Two; fused laterally; ellipsoidal; dorsifixed, longitudinal; about 2.0 mm long and about 1.0 mm across; color along dehiscence separation line nearest RHS 61A, elsewhere nearest RHS 73A.

*Pollen*.—Abundant, elliptic to globose, less than 0.1 mm; color nearest RHS 18B.

Gynoecium: Single; exserted; about 4.2 cm long;

*Style*.—Terete; about 3.9 cm by about 0.5 mm; exserted beyond hood at anthesis; color base nearest RHS NN155D, distal one-third developing tinting increasing at distal end to nearest RHS 71D.

*Stigma*.—Bifid in the distal 2.0 mm, less than 0.25 mm in diameter; color nearest RHS 71D.

*Ovary*.—Ellipsoidal; about 1.0 mm by about 0.75 mm; color between RHS 143D and RHS 144B.

Calyx: Fused in long tube forming corolla; about 9.5 mm long and 3.0 mm across at apex and tube portion about 2.0 mm diameter;

Sepals: Five; ciliolate margin; apiculate to narrowly acute apex; basal 8.5 mm fused, split in about the apical 1.5 mm, about 1.0 mm at fusion;

Sepal color: Abaxial base nearest RHS 155A transitioning to nearest RHS 138B with veins and apices nearest RHS 138A; adaxial base nearest RHS 145D transitioning to nearest RHS 145A with veins and apices between RHS 138B and RHS 138A;

Peduncle: Pubescent; stiff; strong; erect; quadrangular; to about 2.0 mm across and about 3.0 cm long above foliage;

Peduncle color: Nearest RHS 144A;

Pedicel: Terete; about 1.0 mm long and about 0.5 mm diameter; color nearest RHS 145D;

Bracts: Five to eight subtending flower head; acute to narrowly acute apex with sessile and truncate base; to about 1.7 cm and about 1.5 cm wide at base, size decreasing distally;

Bract color: Lowest bracts same color as leaves; distally abaxial and adaxial becoming blushed with nearest RHS N77B; veins color variable, both surfaces same color as surrounding bract to midribs of nearest RHS 145C, or sometimes adaxial nearest RHS 187B;

Fruit: Single nutlet, elliptical, about 1.0 mm long and 0.7 mm wide;

Hardiness: The new plant grows best with plenty of moisture and adequate drainage; hardy to at least from USDA zone 4 through 8.

Disease and pest resistance: Demonstrated powdery mildew resistance in side by side comparison at least equal to the comparison plants.

I claim:

1. A new and distinct cultivar of ornamental bee balm plant, *Monarda* 'Electric Neon Pink', as herein described and illustrated.

* * * * *